United States Patent
Cupp et al.

(10) Patent No.: US 8,455,005 B2
(45) Date of Patent: Jun. 4, 2013

(54) METHOD AND COMPOSITIONS FOR IMPROVING ANIMAL HEALTH

(75) Inventors: Carolyn Jean Cupp, Liberty, MO (US); Gerardo Perez-Camargo, Cachy (FR)

(73) Assignee: Nestec S.A., Vevey (CH)

( * ) Notice: Subject to any disclaimer, the term of this patent is extended or adjusted under 35 U.S.C. 154(b) by 449 days.

(21) Appl. No.: 12/911,896

(22) Filed: Oct. 26, 2010

(65) Prior Publication Data

US 2011/0038983 A1 Feb. 17, 2011

Related U.S. Application Data

(62) Division of application No. 10/548,418, filed as application No. PCT/US2004/008230 on Mar. 18, 2004, now Pat. No. 7,846,482.

(60) Provisional application No. 60/320,016, filed on Mar. 18, 2003.

(51) Int. Cl.
| | |
|---|---|
| *A61K 35/20* | (2006.01) |
| *A61K 9/00* | (2006.01) |
| *A61Q 11/00* | (2006.01) |
| *A01N 25/34* | (2006.01) |
| *A61K 47/42* | (2006.01) |
| *A23K 1/18* | (2006.01) |

(52) U.S. Cl.
USPC ............. 424/535; 424/49; 424/400; 424/408; 424/439; 426/2

(58) Field of Classification Search
USPC ................. 424/49, 400, 408, 439, 535; 426/2
See application file for complete search history.

(56) References Cited

U.S. PATENT DOCUMENTS

| | | | |
|---|---|---|---|
| 4,956,186 | A | 9/1990 | Streiff et al. |
| 5,011,679 | A | 4/1991 | Spanier et al. |
| 5,114,704 | A | 5/1992 | Spanier et al. |
| 5,227,154 | A | 7/1993 | Reynolds |
| 5,296,217 | A | 3/1994 | Stookey |
| 5,618,518 | A | 4/1997 | Stookey |
| 5,833,953 | A | 11/1998 | Berrocal et al. |
| 6,080,419 | A | 6/2000 | Stookey |
| 6,458,402 | B1 | 10/2002 | Chang |
| 2004/0037944 | A1 | 2/2004 | Cupp et al. |

FOREIGN PATENT DOCUMENTS

CN 1259340 7/2000

OTHER PUBLICATIONS

Beighton et al., "Bacteriological Studies of the Effects of Cow's Milk on Dental Plaque and Dental Caries in Rats", Department of Conservative Dentistry, University of Melbourrne, Parkville 3054, Victoria, Australia, Oct. 1979; vol. 47 (2) pp. 255-262.

Manji et al. 1988. The Role of Protein Denaturation, Extent of Proteolysis, and Storage Temperature on the Mechanism of Age Gelation in a Model System, Journal of Dairy Science, vol. 71, pp. 1455-1463.

*Primary Examiner* — Jon P Weber
*Assistant Examiner* — Kailash C Srivastava
(74) *Attorney, Agent, or Firm* — K&L Gates LLP

(57) ABSTRACT

Products as well as methods for reducing plaque in a domestic animal are provided. The product comprises retorted milk.

21 Claims, No Drawings

METHOD AND COMPOSITIONS FOR IMPROVING ANIMAL HEALTH

CROSS REFERENCE TO RELATED APPLICATIONS

This application is a divisional of U.S. Non-Provisional application Ser. No. 10/548,418, filed Feb. 13, 2006, now U.S. Pat. No. 7,846,482 B2 issued 7 Dec. 2010, which is a U.S. National phase of PCT/US04/08230 that was filed on Mar. 18, 2004, which claims priority to U.S. Provisional Application No. 60/320,016 filed on Mar. 18, 2003 the content of which is expressly incorporated herein by reference thereto.

BACKGROUND OF THE INVENTION

The invention relates generally to a method for reducing and/or preventing the buildup of plaque and calculus, commonly called tartar, on the teeth of domestic animals.

Plaque is formed as a result of bacteria living in the mouth. Bacteria live on remnants of food in the mouth. When bacteria combine with saliva and food debris in the channel between the tooth and gum, plaque forms and accumulates on the tooth. When bacteria continue to grow in the plaque and, as calcium salts are deposited, the plaque hardens to become a limestone-like material called calculus or tartar. In many animals, especially cats and dogs, plaque and tartar accumulation is associated with inflammation of the gums (gingivitis) and can progress to severe periodontal disease. Some animals, especially cats, have been found to have a hypersensitivity or allergic reaction and are called 'plaque-intolerant'. This results in a disease called lymphocytic-plasmacytic gingivitis stomatitis, which affects the entire mouth. In this disease, severe inflammation occurs where the tooth meets the gum line. Chronic gingivitis, periodontitis, and stomatitis can cause severe pain. The animal's behavior may change—irritability, aggressiveness, depression or reclusiveness may be seen. The cat may drool excessively, have difficulty eating or not eat at all. They may have bad breath and may not be grooming themselves adequately. Their gums bleed very easily.

Accordingly, it's essential to remove all plaque and calculus and keep it off. This may be accomplished by daily brushing or the use of plaque controlling products such as chlorhexidine gels and rinses. Unfortunately, even with this intensive care, the disease may progress. Perhaps, the only way to cure the disease and eliminate the very painful lesions may be to extract the teeth. In cases of juvenile onset gingivitis, professional teeth cleaning every 2 months and once—to twice—daily brushing at home for the first year or so of their life, may allow them to revert to a more normal status as they age. Of course, brushing the teeth of an animal is extremely difficult and time consuming.

Other methods for reducing plaque include the daily application of inhibitors that interfere with the calcification of dental plaque by saliva. Such crystal growth inhibitors include soluble pyrophosphates, sodium tripolyphosphate, soluble diphosphonates and certain zinc compounds, such as zinc chloride. U.S. Pat. No. 5,296,217 discloses the use of sequestering agents that are applied as coatings to dry dog food. Such sequestering agents form soluble calcium complexes in saliva and dental plaque fluids to prevent further plaque growth. The preferred sequestering agent disclosed in the '217 patent is sodium hexametaphosphate (HMP) used at levels from 0.5 to about 3.0% by weight of the dry dog food.

U.S. Pat. No. 5,618,518 discloses a variety of chew products, such as a rawhide chew product, which are provided with HMP to reduce the buildup of dental calculus by chewing for an extended period of time. Other rawhide products are disclosed in U.S. Pat. Nos. 5,114,704 and 5,011,679 in which inorganic pyrophosphate compounds are coated on the rawhide product.

U.S. Pat. No. 6,080,419 provides a method to prevent, inhibit, or reduce dental calculus deposits or formation on the teeth of a dental calculus forming animal comprising exposing the teeth to a food product comprising an acidulent amount of phosphoric acid, wherein said food product further comprises an amount of a polycarboxylic acid sequestering agent effective to prevent, inhibit, or reduce dental calculus deposits or formation.

Milk products and milk components have been reported to inhibit bacteria in the mouth that contribute to dental caries in certain animal species such as rodents and humans. For example, U.S. Pat. No. 5,833,953 discloses the reduction of caries through the use of cow's milk which contains fluorine salts.

SUMMARY OF THE INVENTION

The invention is directed to a method for reducing and/or preventing the buildup of plaque and calculus, commonly called tartar, on the teeth of domestic animals, especially cats. The invention is further directed to pet food additives to reduce and/or prevent the buildup of dental plaque and calculus. More specifically, the invention is directed to the use of milk either by itself or as an additive to pet food to reduce and/or prevent such buildup. By adding milk, either as a liquid or as a dried powder, to a domestic animal food product, reduction and/or prevention of dental plaque and calculus can be accomplished. In other words, the invention relates to the use of milk as a food additive to domestic pet food. The milk can be added by the pet food manufacturer or it can be added by the pet owner. Preferably, the milk contains no more than a minor amount of lactose. Further, it is preferable that the milk has been subjected to a retorting process. In an embodiment, the milk is substantially free of lactose.

In an embodiment, the present invention provides a method of treating plaque and calculus build up in a domestic animal comprising the steps of administering to a domestic animal having plaque and calculus build up a therapeutically-effective amount of a product including retorted milk.

In an embodiment, the present invention provides a method for preventing plaque and calculus build up in a companion animal comprising the steps of administering to the companion animal on at least a regular basis a product that provides at least 70 grams per day of retorted milk.

In an embodiment, the present invention provides a nutritional product for providing dental benefits to a domestic animal comprising retorted milk in a liquid form and less than 2.5% lactose on a dried weight basis.

In an embodiment, the present invention provides a nutritional dental product for a domestic animal comprising a pet food having a uniform coating composed of dried milk powder.

In an embodiment, the present invention provides a nutritional product for providing dental benefits to a domestic animal comprising retorted milk in a dry form.

In an embodiment, the present invention provides a method of providing dental treatments to a pet comprising the steps of adding to a pet's diet a dried product including retorted milk.

In an embodiment, the present invention provides a method for producing a dental product for a domestic animal comprising the steps of: retorting milk by heating milk to at least 250° F.; and providing a therapeutically-effective amount of the retorted milk in a form that can be administered to the domestic animal.

Additional features and advantages of the present invention are described in, and will be apparent from, the following Detailed Description of the Invention.

DETAILED DESCRIPTION OF THE INVENTION

The invention is directed to a method for reducing and/or preventing the buildup of plaque and calculus, commonly called tartar, on the teeth of domestic animals, especially cats. The invention is further directed to pet food additives to reduce and/or prevent the buildup of dental plaque and calculus. More specifically, the invention is directed to the use of milk either by itself or as an additive to pet food to reduce and/or prevent such buildup. By adding milk, either as a liquid or as a dried powder, to a domestic animal food product, reduction and/or prevention of dental plaque and calculus can be accomplished. In other words, the invention relates to the use of milk as a food additive to domestic pet food. The milk can be added to the pet food by the pet food manufacturer or it can be added by the pet owner in an amount effective to reduce or prevent the growth of plaque and calculus. The milk may further be use in a method of reducing the incidence of bad breath in a cat, or of reducing or preventing gingivitis and other periodontal diseases.

Although the invention contemplates the addition of milk in its liquid form, the milk can be added in dried form. Further, the invention contemplates the addition of lactase in an amount sufficient to reduce the lactose content to less than about 16%, preferably 2.5%, on a dry matter basis. In preferred embodiments, lactose is present in an amount of from about 0.05% to about 0.5% by weight.

Typically, the milk has a composition comprising whole milk powder, water and lactase. Supplemental calcium may also be included to provide a total calcium content from about 0.05% to about 2% on a dry matter basis. Minor ingredients may include sodium caseinate and sucrose. An example of milk that can be added to a domestic animal's diet is Felix® cat milk. Felix cat milk is sold in Europe by Nestlé Purina PetCare Company.

In one embodiment, the dried powder form of milk can be applied to petfood as a coating. The liquid milk formula is evaporated to produce a dry powder having a moisture content less than about 12%, preferably from about 1% to 10%. The dry milk powder is applied to a petfood kibble by utilizing a standard industry dry powder coating system, such as a tumble coater or powder depositer. The surface of the kibble being slightly tacky or sticky due to previous coatings of any one or a combination of fat, tallow, digest, oil, sugar, hydrocolloid or a meat, poultry or fish-slurry that is applied by known liquid application systems such as spray nozzle, tumble coating or liquid flow which causes the milk powder to adhere to the kibble. The kibble is kept in the tumbling machine for a period of time to create a coating of milk powder which encases the kibble in a uniform or non-uniform manner as desired. In an alternative embodiment, the petfood kibble can be spray coated with a milk powder having any one or a combination of water, oil, tallow, digest, sugar, hydrocolloid, meat, poultry, or a fish-slurry.

In one embodiment of the invention, the milk to be provided to the animal has undergone a retorting process. In an example of such a process, a 100 g container of milk is heated to a temperature of at least 115 C (250° F.) for from about 5 to about 12 minutes.

The methods of the present invention are useful for reducing and/or preventing plaque and calculus in a variety of animals. While the present invention can be utilized to treat wild animals, preferably the invention will be used in the treatment of domestic animals, such as companion animals, for example, dogs and cats.

The methods of the invention are further useful for obtaining additional benefits in a pet, for example an improvement in grooming and the amelioration of unwelcome character traits, such as aggressiveness, reclusiveness, irritability and depression as well as reduced food intake.

The method contemplates administering to an animal a therapeutically-effective amount of milk to reduce and/or prevent plaque and calculus either directly or adding an effective amount of milk to an animal's normal diet to reduce and/or prevent plaque and calculus. This amount can vary depending on the size of the animal and length of treatment. For example, in an embodiment, the animal should consume at least 70 grams of milk per day. In another embodiment, the milk should comprise at least 20% of the total caloric intake of the animal. In another embodiment, the treatment should last at least 7 days and in an embodiment, at least 21 days. However, it is envisioned that the product can be provided as a prophylaxis treatment in which case it would be administered every day, or at least as often as possible, or on a regular basis, e.g., every other day, every third day. The diet to which an effective amount of milk could be added includes dry pet food, moist pet food or semi-moist pet food. Such foods typically contain up to 50% protein, up to 25% fat and up to 5% fiber. The milk could also be added to pet snacks especially pet snacks which are intended to supplement the normal diet and especially those snacks that help in the removal of dental plaque by the normal chewing process. Accordingly, in a preferred embodiment of the invention milk, either in liquid or dried form, is added at least twice daily to food that is provided to an animal to provide the animal with its daily nutritional requirements. Another embodiment of the invention contemplates adding milk, either in liquid or dried form, to snack foods which supplement the animal's regular diet.

The invention can be further characterized by the following example. The example is provided merely to illustrate the benefits of the invention and not as any limitation as to the scope thereof.

Example thirteen cats between the ages of 4 and 17 years were assigned to a trial, which was conducted as a complete crossover design. Assigned dietary treatment groups were 1) Pro Plan® dry cat food alone, and 2) dry Pro Plan® plus Felix Cat Milk. Pro Plan dry cat food is manufactured by Nestlé Purina PetCare Company. Cats were fed their assigned diets for 21 days for each phase of the crossover. Cats were fed dry food to cover their energy requirements and were offered 2 pouches of cat milk daily when on the milk phase. Each pouch contained approximately 130-150 grams of milk. Water was available at all times and water intake was also recorded. Cats were housed in individual stainless steel cages for the duration of the trial. Food, milk, and water intake were recorded daily, and body weight monitored weekly.

An oral exam was conducted on each cat prior to selecting it for the trial. Cats with known or observed dental/oral problems (e.g. marked degree of gingivitis/stomatitis, severe odontoclastic resorptive lesions, multiple missing teeth, etc.) were not selected. Subjective severity of calculus (scale of 0-4) was recorded on initial physical exam form.

Severity of calculus was done by assigning a whole mouth calculus score of 0 to 4 to cats who had not had dental prophylaxis for a year. Subjective calculus scores were assigned as follows:

| | |
|---|---|
| 0 = | No calculus |
| 1 = | Mild calculus buildup |
| 2 = | Moderate calculus buildup |
| 3 = | Marked calculus buildup |
| 4 = | Severe calculus buildup |

Both sides of the mouth were scored and the overall score assigned represents an average of the two sides. Initial severity of calculus was used in blocking the cats to initial treatment groups.

Complete dental prophylaxis (ultrasonic cleaning and polishing) was performed on all cats on day 0 under anesthesia. A UV light was used to insure that all plaque and tartar was removed by the prophylaxis after cleaning and before polishing. A single examiner conducted all dental evaluations. Dental examiner "blindness" was maintained throughout the trial. Randomization of cats to dietary treatment groups was performed by the Nestlé Purina statistician. Pet care technicians were responsible for assigning diets to groups at the beginning of the trial and performed all animal handling, feeding, and daily management of the cats on trial. A licensed veterinary technician assured that cats were evaluated in random order during the dental scoring.

On day 21, cats were anesthetized as on day 0 and a 3% erythrosin plaque-disclosing solution was applied to the teeth, rinsed with tap water, and an evaluation of plaque recorded. For plaque scoring, each tooth evaluated (buccal side only) was visually divided into horizontal halves, "gingival" and "occlusal". Each half was given a numerical score to indicate percent plaque coverage of the tooth as follows for a total of 28 scores per cat with the following scoring method (coverage×thickness):

| Coverage thickness | |
|---|---|
| 0 = | No plaque 1 = light (light pink) |
| 1 = | <25% 2 = medium (medium red) |
| 2 = | 25-49% 3 = heavy (dark, bright red) |
| 3 = | 50-74% |
| 4 = | 75-100% |

Plaque was then gently brushed away with a toothbrush, rinsed with a forced stream of water, and air-dried. For calculus scoring, teeth were visually divided into vertical thirds, mesial, buccal and distal. Each third was given a numerical score to indicate percent calculus coverage of the tooth as follows for a total of 42 scores per cat with the following scoring method (coverage×thickness):

| Coverage thickness | |
|---|---|
| 0 = | No calculus 1 = light |
| 1 = | <25% 2 = moderate |
| 2 = | 25-49% 3 = heavy |
| 3 = | 50-74% |
| 4 = | 75-100% |

Complete dental prophylaxis was performed again after plaque and calculus scoring was complete, again using a UV light to insure no remaining plaque/calculus was left on the teeth.

On day 42, cats were sedated again, and plaque and calculus scoring repeated as listed above. Dental score data were analyzed using analysis of variance to test for differences between diets. For plaque and calculus scores, a total tooth score analysis was made, which reflects a summation of two or three scores per tooth to yield whole tooth scores. These scores were then averaged across teeth of all cats on each diet to obtain overall group scores. The results are summarized in Table 1 below.

Dental Efficacy. At the end of 21 days, mean overall (total tooth) plaque scores for all cats were as follows.

TABLE 1

| Product | Mean | Std. Error |
|---|---|---|
| Pro Plan ® dry cat (control) | 6.23 | 0.17 |
| Pro Plan ® dry cat + Felix Cat Milk | 5.56 | 0.17 |

The group of cats that consumed milk had 12% less plaque than cats in the control group (p<0.01). At the end of 21 days, mean overall (total tooth) calculus scores for all cats were as follows:

TABLE 2

| Product | Mean | Std Error |
|---|---|---|
| Pro Plan ® dry cat (control) | 2.52 | 0.27 |
| Pro Plan ® dry cat + Felix Cat Milk | 1.76 | 0..27 |

The group of cats that consumed milk has 30% less calculus than cats in the control group (p<0.01).

Food and Milk Consumption

The average milk consumption during the trial for all cats was 117.67 grams per day. The average milk consumption ranged from 48-155 gm per cat.

The average food consumption in the control group was 57.33 grams of dry cat food per day.

The average food consumption in the milk group was 43.40 grams of dry cat food per day.

It is apparent from the foregoing Example that providing cats with milk, especially milk that has been retorted can significantly reduce plaque and calculus. Having described the invention in detail, those skilled in the art will appreciate that modifications may be made of the invention without departing from its spirit and scope. Therefore, it is not intended that the scope of the invention be limited to the specific embodiments described.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of providing dental treatments to a companion animal comprising the steps of adding to a companion animal's diet a product including a therapeutically-effective amount of retorted milk.

2. The method of claim 1 wherein the product is administered to the domestic animal for at least 21 days.

3. The method of claim 2 wherein the companion animal receives sufficient product so as to provide at least 20% of the companion animal's total daily caloric needs as retorted milk.

4. The method of claim 3 wherein the companion animal is selected from the group consisting of a dog and a cat.

5. The method of claim 1 wherein the product comprises a substrate to which a coating including the retorted milk has been applied.

6. The method of claim 5 wherein the substrate is a pet food kibble.

7. The method of claim 1 wherein the product is produced by a method comprising the steps of:
retorting milk by heating milk to at least 250° F.; and
providing a therapeutically-effective amount of the retorted milk in a form that can be administered to the domestic animal.

8. The method of claim 7 wherein the retorted milk is dried to a powder.

9. The method of claim 7 including the step of adding lactase to the milk to reduce the lactose content.

10. The method of claim 7 including the step of coating the retorted milk around an edible substrate.

11. The method of claim 7 including the step of adding calcium to the retorted milk product.

12. The method of claim 1 wherein the product is a pet snack.

13. The method of claim 1 wherein the dental treatment is for the prevention of plaque and calculus build up in a companion animal.

14. The method of claim 1 wherein the product is in a liquid form.

15. The method of claim 1 wherein the product is in a dried form.

16. The method of claim 1 wherein the product is a nutritional supplement to a standard diet of the domestic animal.

17. The method of claim 1 wherein the companion animal is selected from the group consisting of a dog and a cat.

18. The method of claim 1 wherein the product includes no more than 0.5% by weight on a dried basis lactose.

19. The method of claim 1 wherein the product provides at least from about 48 grams to about 155 grams of retorted milk per day.

20. The method of claim 1 wherein the product comprises a substrate to which a coating including the retorted milk has been applied.

21. The method of claim 1 wherein the substrate is a pet food kibble.

* * * * *